(12) United States Patent
Seidel

(10) Patent No.: US 6,342,619 B2
(45) Date of Patent: *Jan. 29, 2002

(54) SYNTHESIS OF CONJUGATED FATTY ACID

(76) Inventor: Michael C. Seidel, 61 Hickory La., Chalfont, PA (US) 18914

( * ) Notice: Subject to any disclaimer, the term of this patent is extended or adjusted under 35 U.S.C. 154(b) by 0 days.

This patent is subject to a terminal disclaimer.

(21) Appl. No.: 09/731,955

(22) Filed: Dec. 7, 2000

Related U.S. Application Data

(63) Continuation-in-part of application No. 09/283,554, filed on Apr. 1, 1999, now Pat. No. 6,160,141.

(51) Int. Cl.$^7$ .................................. C11C 3/00
(52) U.S. Cl. ................................... 554/126
(58) Field of Search ......................... 554/126

(56) References Cited

U.S. PATENT DOCUMENTS 5,892,074 A * 12/2000 Seidel ................. 554/126
6,160,141 A * 12/2000 Seidel ................. 554/126

* cited by examiner

Primary Examiner—Deborah D. Carr
(74) Attorney, Agent, or Firm—Douglas G. Glantz

(57) ABSTRACT

A synthesis process is disclosed for producing a conjugated fatty acid at specified temperature in high yield, including providing an ester of a fatty acid having somewhere in its carbon chain a chain of four carbon atoms such that carbon one bears one hydrogen and one hydroxyl group, carbon two bears two hydrogen atoms, and a double bond is positioned between carbon three and carbon four and reacting with a chloride selected from the group consisting of toluenesulfonyl chloride, methanesulfonyl chloride, benzenesulfonyl chloride, alkylsulfonyl chloride, and arylsulfonyl chloride at a temperature in the range of 10° C.–100° C., preferably 20° C.–50° C. The synthesis process provides a conjugated fatty acid formed from the ester reacted with diazabicycloundecene. In one aspect, the ester is formed in a pyridine solvent. In one aspect, a mesylate is formed with mesyl chloride in acetonitrile and triethyl amine. In one aspect, the reaction with diazabicyclo-undecene is conducted in a polar, non-hydroxylic solvent of acetonitrile to form a preferred isomer at the specified temperature in high yield.

20 Claims, 5 Drawing Sheets

SYNTHESIS OF CONJUGATED FATTY ACID

This patent application is a continuation-in-part of U.S. patent application Ser. No. 09/283,554, filed Apr. 1, 1999, now U.S. Pat. No. 6,160,141.

BACKGROUND OF THE INVENTION

1. Technical Field

This invention relates to a synthesis of conjugated fatty acid. In one aspect, this invention relates to a novel synthesis to form a high purity conjugated fatty acid.

2. Background

Conjugated linoleic acid (CLA) is a general term used to name positional and geometric isomers of linoleic acid.

Conjugated eicosadienoic acid (CEA) is a general term used to name positional and geometric isomers of the C-20 fatty acid of 11-cis, 13-trans eicosadienoic acid, also known as 11(Z),13(E)-eicosadienoic acid.

Linoleic acid and eicosadienoic acid are straight chain carboxylic acids having double bonds between the ninth and tenth, twelfth and thirteenth carbons and eleventh and twelfth, fourteenth and fifteenth carbons, respectively. Linoleic acid is 9-cis, 12-cis octadecadienoic acid [9(Z),12(Z)-octadecadienoic acid]. The numbers are counted from the carboxylic acid moiety. See Formula (1) for 9-cis, 12-cis octadecadienoic acid [9(Z),12(Z)-octadecadienoic acid]. See Formula (2) for 11-cis, 13-trans eicosadienoic acid, [11(Z),13(E)-eicosadienoic acid].

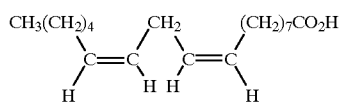

(1)

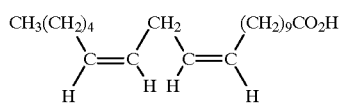

(2)

Conjugated linoleic acid (CLA) has two conjugated double bonds between the ninth and the twelfth carbons or between the tenth and thirteenth carbons, with possible cis and trans combinations. Conjugated eicosadienoic acid (CEA) has two conjugated double bonds between the eleventh and fourteenth or between the twelfth and fifteenth carbons, with possible cis and trans combinations. Conjugated double bonds means two or more double bonds which alternate in an unsaturated compound as in 1,3 butadiene. The hydrogen atoms are on the same side of the molecule in the case of cis. The hydrogen atoms are on the opposite side of the molecule in the case of trans. See Formula (3) for conjugated linoleic acid (CLA). See Formula (4) for conjugated eicosadienoic acid (CEA).

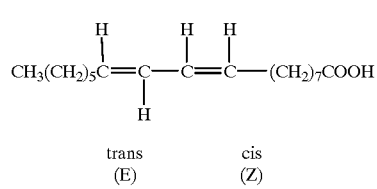

(3)

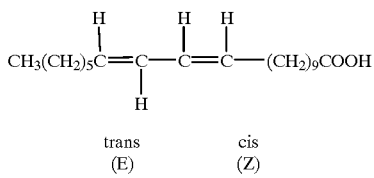

(4)

The free, naturally occurring conjugated linoleic acids (CLA) have been previously isolated from fried meats and described as anticarcinogens by Y. L Ha, N K. Grimm and M. W. Pariza, in Carcinogenesis, Vol. 8, No. 12, pp. 1881–1887 (1987). Since then, they have been found in some processed cheese products (Y. L. Ha, N. K. Grimm and M. W. Pariza, in J. Agric. Food Chem., Vol. 37, No. 1, pp. 75–81 (1987)).

The free, naturally occurring conjugated eicosadienoic acids (CLA) are not known to exist.

Cook et al. in U.S. Pat. No. 5,554,646 disclose animal feeds containing CLA, or its non-toxic derivatives, e.g., such as the sodium and potassium salts of CLA, as an additive in combination with conventional animal feeds or human foods. CLA makes for leaner animal mass.

INTRODUCTION TO THE INVENTION

The free acid forms of CLA may be prepared by isomerizing linoleic acid. The terms "conjugated linoleic acids" and "CLA" as used herein are intended to include 9,11-octadecadienoic acid, 10,12-octadecadienoic acid, mixtures thereof, and the non-toxic salts of the acids. The non-toxic salts of the free acids may be made by reacting the free acids with a non-toxic base.

Historically, CLA was made by heating linoleic acid in the presence of a base. The term CLA (conjugated linoleic acid) refers to the prior art preparation involving alkali cooking of linoleic acid.

A conventional method of synthesizing CLA is described in Example I. However, CLA also may be prepared from linoleic acid by the action of a linoleic acid isomerase from a harmless microorganism, such as the Rumen bacterium *Butyrivibrio fibrisolvens*. Harmless microorganisms in the intestinal tracts of rats and other monogastric animals may also convert linoleic acid to CLA (S. F. Chin, J. M. Storkson, W. Liu, K. Albright and M. W. Pariza 1994, J. Nutr., 124; 694–701).

The prior art method of producing conjugated linoleic acids (CLA) can be seen in the following Example I using starting materials of linoleic acid or safflower oil.

EXAMPLE I

Synthesis of Conjugated Linoleic Acids (CLA) from Linoleic Acid/Safflower Oil

Ethylene glycol (1000 g) and 500 g potassium hydroxide (KOH) are put into a 4-neck round bottom flask (5000 ml). The flask is equipped with a mechanical stirrer, a thermometer, a reflux condenser, and a nitrogen inlet. The nitrogen to be introduced is first run through two oxygen traps.

Nitrogen is bubbled into the ethylene glycol and KOH mixture for 20 minutes, and the temperature is then raised to 180° C.

1000 g of linoleic acid, corn oil, or safflower oil is then introduced into the flask. The mixture is heated at 180° C. under an inert atmosphere for 2.5 hours.

The reaction mixture is cooled to ambient conditions, and 600 ml HCL are added to the mixture which is stirred for 15 minutes. The pH of the mixture is adjusted to pH 3. Next, 200 ml of water is added into the mixture and stirred for 5 minutes. The mixture is transferred into a 4 L separatory funnel and extracted three times with 500 ml portions of hexane.

The aqueous layer is drained, and the combined hexane solution is extracted with four 250-ml portions of 5% NaCl solution.

The hexane is washed 3 times with water. The hexane is transferred to a flask, and the moisture in the hexane is removed with anhydrous sodium sulfate ($Na_2SO_4$). The hexane is filtered through Whatman paper into a clean 1000 ml round bottom flask, and the hexane is removed under vacuum with a rotoevaporator to obtain the CLA. The CLA is stored in a dark bottle under argon at −80° C. until time of use.

The CLA obtained by the practice of the described prior art methods of preparation typically contains two or more of the 9,11-octadecadienoic acids and/or 10–12-octadecadienoic acids and active isomers thereof. After alkali treatment, the compound may be in the free acid or salt form. The CLA is heat stable and can be used as is, or it may be dried in a solvent. The CLA is readily converted into a non-toxic salt, such as the sodium or potassium salt, by reacting chemically equivalent amounts of the free acid with an alkali hydroxide at a pH of about 8 to 9.

Theoretically, eight (8) possible geometric isomers of 9,11 and 10,12-octadecadienoic acid (c9,c11; c9,t11; t9,c11; t9,t11; c10,c12; c10,t12; t10,c12; and t10,t12) would form from the isomerization of c9,c12 octadecadienoic acid. As a result of the isomerization, only four isomers (c9,c11; c9,t11; t10,c12; and c10,c12) would be expected. Because of double bond shifts, more isomers are produced. A total of twelve isomers have been identified so far. However, of the four isomers, c9,t11- and t10,c12- isomers are predominantly produced during the autoxidation or alkali isomerization of c9,c12-linoleic acid because of the co-planar characteristics of 5 carbon atoms around a conjugated double bond and spatial conflict of the resonance radical. The remaining two c,c-isomers are minor contributors as are the other isomers.

The relatively higher distribution of the t,t-isomers of 9,11- or 10,12-octadecadienoic acid apparently results from the further stabilization of c9,t11- or t10,c12-geometric isomers, which is thermodynamically preferred, during an extended processing time or long aging period. Additionally, the t,t-isomer of 9,11- or 10,12-octadecadienoic acid predominantly formed during the isomerization of linoleic acid geometrical isomers (t9,t12-, c9,t12-, and t9,c12-octadecadienoic acid) may influence the final ratio of the isomers or the final CLA content in the samples.

Linoleic acid geometrical isomers also influence the distribution of minor contributors (c,c-isomers of 9,11- and 10,12-, t9,c11- and c11,t12-octadecadienoic acids). The 11,13-isomer might be produced as a minor product from c9,c12-octadecadienoic acid or from its isomeric forms during processing.

Conjugated linoleic acid (CLA) has long been of interest to 10 biochemists and nutritionists. A recent article in INFORM, Vol. 7, No. 2, February 1996, published by the American Oil Chemists' Society summarizes some of the data developed so far. The article stresses the feed use for which the product is currently being developed, resulting in less fat and more lean meat in animals. A number of other recent articles stress effects in fighting cancer. In many cases, one isomer, 9(Z),11(E)-CLA, has been named as the active isomer, mainly because it alone is incorporated into the phospholipids of the organism being fed CLA.

CLA has been shown to have preventive effects on breast cancer in mice. CLA is not used for humans today, mostly because it is not available except in impure forms. CLA is not approved by the FDA, and impurities can have a detrimental influence on toxicity tests to obtain FDA approval.

The problem with CLA, as it is available today, has been the fact that only a diverse mixture of isomers can be made. Conventional synthesis methods involve the isomerization of linoleic acid by potassium hydroxide at about 200° C. This procedure yields about equal amounts of the 9,11- and 10,12-isomers which are almost impossible to separate. The content of the preferred isomer of 9(Z),11(E)-CLA in the mix is about 20–30%. All of the isomers presumed to be in the mix have been synthesized but only by very laborious methods that are quite unsuitable for large scale manufacture.

Heating the linoleic acid in the presence of a base such as alkali, makes the double bond move over, and it does so in a haphazard way. The geometry changes, and the resultant product is the 9-cis, 11-trans isomer in a yield of only 23–40%.

The problem with conjugated eicosadienoic acid (CEA), is that it is not available today, i.e., free, naturally occurring conjugated eicosadienoic acids (CLA) are not known to exist.

Lesquerella oil is a rare plant seed oil. Seeds of lesquerella plants contain hydroxy fatty acids. Lesquerella oil is available only in very low quantities because there is no commercial crop to speak of. The very low quantities of lesquerella oil have inhibited product and market development.

Lesquerella oil can be hydrolyzed to form lesquerolic acid. The lesquerolic acids are hydroxy fatty acids. The major (about 50%) hydroxy fatty acid is 14-hydroxy-cis-11, cis-17-eicosenoic acid (lesquerolic acid), a homolog of ricinoleic acid. Hydrolyzed lesquerella oil contains an amount of about 3% of 14-hydroxy-cis-11, cis-17-eicosadienoic acid.

It is an object of the present invention to provide a novel synthesis of conjugated fatty acid.

It is an object of the present invention to provide a novel synthesis of over 50 per cent pure conjugated fatty acid.

It is an object of the present invention to provide a novel synthesis of over 70 per cent pure conjugated fatty acid.

It is an object of the present invention to provide a novel synthesis of conjugated fatty acid at preferred temperatures.

It is an object of the present invention to provide a novel synthesis of higher yield and purity conjugated fatty acid than is available from conventional sources containing impurities which may have a detrimental influence on toxicity tests to obtain FDA approval.

It is an object of the present invention to provide a novel synthesis of conjugated fatty acid than is available from conventional sources containing diverse mixtures of isomers which have a detrimental influence on toxicity tests to obtain FDA approval.

These and other objects of the present invention will be described in the detailed description of the invention which follows. These and other objects of the present invention will become apparent from a careful review of the detailed description and from reference to the figures of the drawings which follow.

SUMMARY OF THE INVENTION

The present invention provides a synthesis for producing conjugated fatty acid. A fatty acid ester is selected having somewhere in its carbon chain a chain of four carbon atoms such that carbon one bears one hydrogen and one hydroxyl group, carbon two bears two hydrogen atoms, and a double bond is positioned between carbon three and carbon four. The fatty acid ester is reacted with a chloride including toluenesulfonyl chloride, methanesulfonyl chloride, benzenesulfonyl chloride, alkylsulfonyl chloride, or arylsulfonyl chloride at a temperature in the range of 10–100° C. to form an alkyl- or aryl-sulfonyl ester. The conjugated fatty acid bearing the alkyl- or aryl-sulfonyl ester is reacted with diazabicyclo-undecene to form a conjugated fatty acid ester having a purity greater than 40%. The conjugated fatty acid is formed in high yield. In one aspect, the sulfonyl ester of a fatty acid ester is formed in a pyridine solvent. In one aspect, the sulfonyl ester of a fatty acid ester is reacted with diazabicyclo-undecene in a polar, non-hydroxylic solvent acetonitrile.

DETAILED DESCRIPTION

Figure 1:
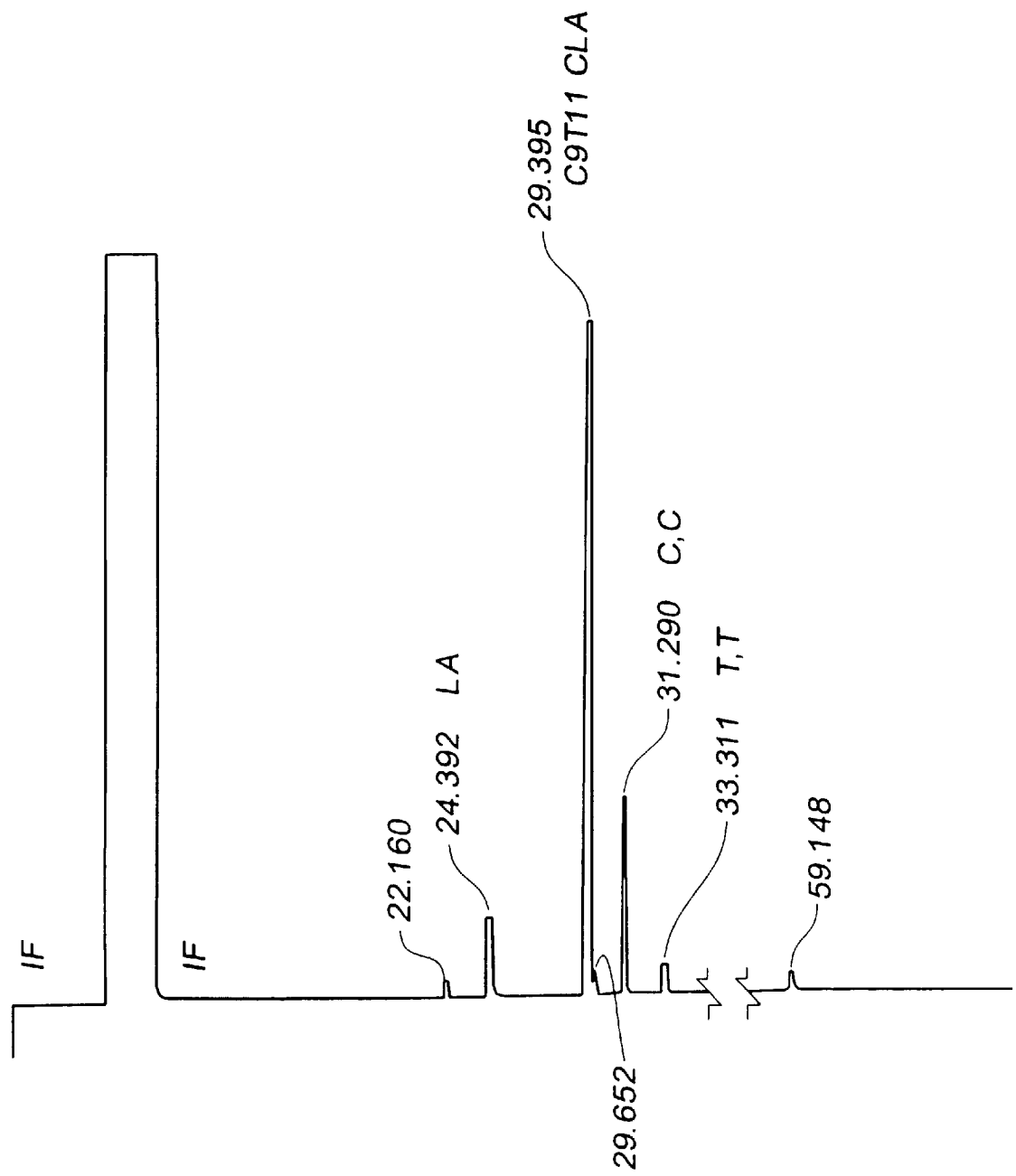
FIG. 1 is a graphical view of a gas chromatography printout of CLA produced by a novel synthesis for purified CLA used in the method of the present invention.

The process of the present invention provides a method for producing a high yield and purity conjugated fatty acid.

In one aspect, the process of the present invention provides a method for producing a high yield and purity conjugated fatty acid using a temperature in the range of 10–100° C., preferably 20–50° C.

In one aspect, the process of the present invention provides a method for producing a high yield and purity conjugated fatty acid using toluenesulfonyl chloride, methanesulfonyl chloride, benzenesulfonyl chloride, alkylsulfonyl chloride, or arylsulfonyl chloride.

The process of the present invention provides a method for producing a high yield and purity conjugated fatty acid having structural features, as suitable starting materials, as shown by materials I and II.

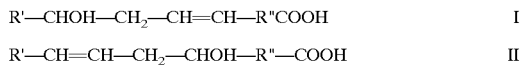

where the double bond can be either cis or trans (Z or E).

R' is defined as $CH_3-(CH_2)_x$ where x is from 1 to 10 with 3 to 7 preferred, and R" is defined as $-(CH_2)_y$ where y is defined as from 1 to 12 with 5 to 9 preferred.

The structural features of I and II are described as "a fatty acid having somewhere in its chain a chain of four carbon atoms such that carbon one bears one hydrogen and one hydroxyl group, carbon two bears two hydrogen atoms, and a double bond is positioned between carbon three and carbon four."

In one aspect, the process of the present invention provides a purified 9-cis, 11-trans octadecadienoic acid formed by a novel synthesis of reacting a methyl ricinoleate with a tosyl chloride or a mesyl chloride to form a tosylate or mesylate of a ricinoleate, and reacting the tosylate or mesylate of a ricinoleate with diazabicyclo-undecene.

The novel synthesis produces conjugated linoleic acid having 40% or more, preferably 50% or more, of the isomer 9-cis, 11-trans octadecadienoic acid.

In one aspect, the process of the present invention provides a purified 11-cis, 13-trans eicosadienoic acid formed by a novel synthesis of reacting a methyl lesquerolate with a tosyl chloride or a mesyl chloride to form a tosylate or mesylate of a lesquerolate, and reacting the tosylate or mesylate of a lesquerolate with diazabicyclo-undecene.

The novel synthesis produces eicosadienoic acid having 40% or more, preferably 50% or more, of the isomer 11-cis, 13-trans eicosadienoic acid.

In one aspect, the process of the present invention provides a purified conjugated fatty acid formed by a novel synthesis of reacting a methyl ester of a fatty acid having somewhere in its chain four carbon atoms such that carbon one bears one hydrogen and one hydroxyl group, carbon two bears two hydrogen atoms, and a double bond is positioned between carbon three and carbon four, with a tosyl chloride or a mesyl chloride to form a tosylate or mesylate, and reacting the tosylate or mesylate with diazabicyclo-undecene to form a conjugated fatty acid.

My novel synthesis can be summarized as follows in this detailed description of the novel synthesis as used in the method of the present invention.

I have found that a preparation of the preferred isomer, e.g., of 9(Z),11(E)-CLA or 11(Z),13(E)-CEA, containing 50% of the desired isomer accompanied by the 9(Z),11(Z)-CLA or 11(Z),13(Z)-isomer, respectively, can be made. From this material, the desired isomer can be separated by low temperature crystallization to give higher purity of the preferred isomer. The following conditions are required for this novel synthesis reaction.

1. Methyl ricinoleate or methyl lesqueroleate is made into the tosylate by reaction in pyridine as solvent. When other solvents are used and pyridine only as reagent, the reaction takes days and even then does not go to completion. I have found the reaction goes to completion overnight with pyridine as solvent at room temperature.

2. The tosylate is reacted with diazabicyclo-undecene (DBU) in acetonitrile as solvent (1 hour reflux) to give a clean complete reaction. Diazabicyclononene (DBN) is more expensive, but it also works. Solvents other than acetonitrile delay completion for many hours leading to side products and incomplete reactions. Other polar but non-hydroxylic solvents may also be useful. Examples of such other polar, non-hydroxylic solvents are dimethyl formamide, dimethyl sulfoxide, or chloroform. Care must be taken to remove traces of the pyridine from the previous step to avoid a substitution reaction. See Equations (5) and (6) and Equations (7) and (8).

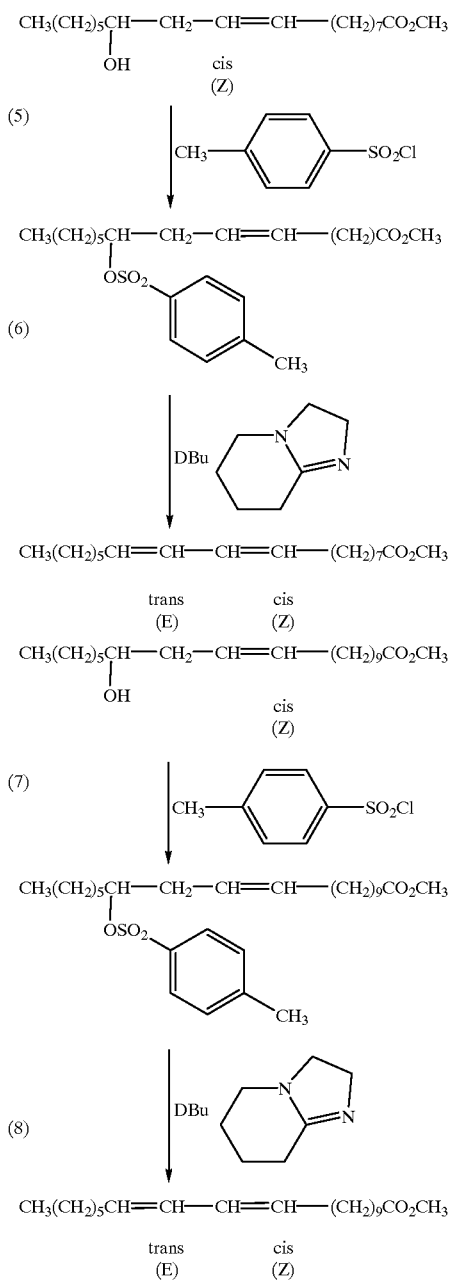

The method for providing a purified conjugated fatty acid of the present invention includes separating the purified conjugated fatty acid by liquid chromatography to provide a purity greater than 50% by weight, preferably greater than 70% by weight, and then separating by liquid chromatography to provide a purity greater than 90% by weight, preferably greater than 95% by weight.

The preferred procedure for producing Conjugated Eicosadienoic Acid (11(Z),13(E)-eicosadienoic acid) in the process of the present invention is as follows.

Methyl Lesquerolate is produced in the process of the present invention in the following manner.
1. Add 10 ml of concentrated sulfuric acid to a mixture of 1.5 kg of Lesquerella oil and 1.3 liters of methanol.
2. Reflux the mixture for 5 hours.
3. Cool mixture to room temperature.
4. Partition the mixture between 600 ml hexane and 1000 ml of saturated sodium chloride solution in which is dissolved 10 g sodium hydroxide.
5. Adjust the pH of the aqueous layer to 6–7 by adding acetic acid.
6. Extract the aqueous layer with 600 ml ethyl ether.
7. Wash the combined organic layers with water twice.
8. Evaporate most organic solvents and the remainder of water under water jet vacuum.
9. Distill the residue under high vacuum (<4 mm Hg), collecting fractions of 250 ml, 250 ml, 500 ml, 1000 ml. Repeat, if necessary. Keep fractions containing more than 83% of methyl lesquerolate.

Tosylated Methyl Lesquerolate is produced in the process of the present invention in the following manner.
1. Mix 915 g of methyl lesquerolate and 1050 ml of pyridine in a 5 liter flask.
2. Cool the flask in an ice bath.
3. After the temperature of the mixture has reached 0–5° C., add 763 g of toluene sulfonyl chloride (tosyl chloride) portion by portion.
4. Stir the mixture at 5–20° C. for 24 hours. Control the temperature with an ice bath.
5. TLC check for completion of the reaction (pet. ether-:ethyl ether 85:15).
6. Partition the reaction mixture between 600 ml hexane and cooled 10% sulfuric acid solution.
7. Wash the organic layer with 10% sulfuric acid solution until the pH of the wash solution is 2–3. Combine the aqueous layers.
8. Wash the organic layer with water twice, discard those aqueous layers.
9. Extract the combined aqueous layers of point (7) with 600 ml hexane once. Combine the organic layers.
10. Wash the combined organic layers with 10% sulfuric acid once, with water twice, and discard the aqueous layers.
11. Dry the organic layer with anhydrous sodium sulfate, filter and evaporate the solvent with a rotatory evaporator. Product is a gold colored liquid.

The Methyl Ester of Conjugated Eicosadienoic Acid is produced in the process of the present invention in the following manner.
1. Add 500 ml of acetonitrile and 650 g of 1,8-diazabicyclo[5,4,0]undecec-7-ene (DBU) to the tosylated methyl lesquerolate.
2. Stir the mixture at room temperature for seven days. Two layers develop in the mix.
3. After TLC (mobile phase as above) indicates a complete reaction, separate the layers in a separatory funnel.
4. Acidify the bottom layer with 10% HCl to a pH of 2–3 and extract with 600 ml of a 50:50 hexane:ethyl ether mixture twice. Discard the aqueous layer and combine all organic layers.
5. Wash the combined organic layers with 10% HCl solution until the pH is 2–4. Then wash twice with water until the pH is 4–6.
6. Dry with sodium sulfate and filter.
7. Evaporate all solvents, and check by TLC and GC. If the product meets QC specifications, convert to acid form.

The Conversion to Acid is performed in the process of the present invention in the following manner.

1. Use 1 mol of ester to 2 moles of potassium hydroxide. Molecular weight of 11(Z),13(E)-C20:2 is 322.5; molecular weight of potassium hydroxide is 56.1. Dissolve the KOH in DI water (3.3 ml/g), and then add to the methanol and ester (methanol: ester 5:1). Reflux for 20–30 minutes; make sure heat is less than 65° C. Check by TLC for completion.
2. Cool to room temperature; adjust pH to 2–4 using 6 N HCl.
3. Add an equal amount of DI water, and extract 2 times with twice the amount of hexane. Combine the hexane extracts and wash with DI water. Dry hexane layer over anhydrous sodium sulfate.
4. Evaporate solvent and remove last traces with a flow of nitrogen.
5. Check by TLC and by GC (as in the case of purified CLA).

The process of the novel synthesis of the present invention was initiated as performed in Example II for the preparation of methyl lesqueroleate.

EXAMPLE II 5 400 g of lesquerella oil was admixed with 600 ml methanol and 3 ml of concentrated sulfuric acid. The mixture was refluxed for 5 hours. TLC (4 pet ether:1 ethyl ether) showed starting oil disappeared. Distilled out about 200 ml of methanol. Cooled the mixture to room temperature, poured it into saturated NaCl solution (1L) and 1.5 g of NaOH in a separatory funnel. Partitioned it between the brine (basic) and pet ether. Gently shaked to prevent emulsion. Separated the aqueous into a flask, repeated the wash in basic brine once. Neutralized the aqueous solution with acetic acid to a pH of 6–7. Extracted the aqueous with pet ether twice and with ethyl ether twice. Combined organic layer was washed thoroughly with brine four times and water once. Checked the pH of washing carefully to make sure it was 6–7. Put into separatory funnel and took the organic layer into a round bottom flask. Distilled the solvent first at 1 atm then at reduced pressure to remove solvent and trace water. Then distilled under high vacuum. Yellow oil first cut and second cut 240 g., 83% of methyl ester. Washed the combined brine with 10% sulfuric acid twice, brine twice, and water twice. Stored in freezer.

EXAMPLE III

Methyl Lesquerolate from Example II in an amount of 242 g (~80%) FW 340 was admixed with NaOH-dried pyridine in an amount of 230 ml 4 eq. 0.71 mole. Cooled the mixture to ~5° C. Added 210 g of tosyl chloride. FW=190. (0.71 mole×1.5 eq.) Stirred the mixture at 10–20° C. for four hours. TLC (25 EE:75 PE) showed ~40%–30% starting material remained. Put ice into the ice bath and immersed the reaction flask overnight. Morning temperature was 22–25° C. Stirred at 10–20° C. for 1 day. TLC checked reaction completed. Partitioned between ether and cold water. Extracted with ether. Washed with 10% sulfuric acid and water. The pH was ~6–7. Dried over magnesium sulfate for 1 day. Filtered removed solvent at room temperature on rotevap.

The mixture was stirred at room temperature (20–30° C., or 25–30° C.) for 10 days. Then warmed at 60–70° C. for 4 hours. TLC showed no tosylate. Partitioned between hexane and 10% sulfuric acid. Separated the organic, washed with 10% sulfuric acid, and water. Extracted aqueous with ethyl ether three times. Then washed the organic with 10% sulfuric acid and brine. Combined the organic with the material from the freezer from Example II.

EXAMPLE IV 1500 g of lesquerella oil were admixed in 1300 methanol and 10 ml of concentrated sulfuric acid, and the mixture was stood at room temperature overnight. The mixture then was refluxed for 5 hours. The mixture was partitioned between NaCl saturated solution and hexane. The pH of the aqueous layer then was adjusted to 6–7 by adding HOAc. The organic layer was washed with saturated NaCl solution and water. The aqueous layer was extracted with ether. The ether layer was washed with brine and water. The combined organic layer was washed with water three times. The pH was ~6–7. The organic layer was distilled at 1 atm to remove solvents, then under reduced pressure to remove water and solvents. Distilled the residue under high vacuum. Found the material decomposed during the distillation. The last drop contained decomposed compounds. Did not get pure lesquerella ester >93%, which indicated the methyl lesquerella ester decomposed in this experiment.

The residue in the distillation pot methyl lesquerella ester (>95%) was refluxed with 500 ml of methanol, 100 ml of 1N NaOH and ~15 g of NaOH. TLC checked hydrolysis completed (20 EE:80 PE:1 AcOH). Partitioned between hexane and 10% sulfuric acid. (The washing was pH<2.) Separated black gum. Repeated washing with 10% sulfuric acid, pet ether, and water. The pet ether removed the black gum, which separated out from solution. Dried over magnesium sulfate. Filtered. Removed the solvents on rotovap under reduced pressure at room temperature. Kept it in dry ice box over weekend.

EXAMPLE V

A mixture of lesquerolate methyl ester (~80–85%, slight yellow-brown distilled, MW 340, 2.68 mole) and pyridine (dry over NaOH, 1050 ml, 13 mole, 4.85 eq.) was stirred at 0–5° C. Added tosyl chloride (FW=190, 763 g, 2.68×1.5 mole) portion by portion. The mixture was stirred at 5–20° C. for 1 day. Partitioned between hexane and 10% sulfuric acid (ice). Washed with 10% sulfuric acid, water. Extracted with hexane. Washed with 10% sulfuric acid, water. Dried over magnesium sulfate/sodium sulfate. Filtered. Obtained clean solution. Evaporated solvent under reduced pressure. Golden yellow solution.

Added 500 ml of AcN and 650 g of DBU. The mixture was stirred at room temperature for 1 week. Worked-up. The mixture was separated into two layers. Each layer was washed with 10% sulfuric acid three times, and extracted the aqueous layer with 1:1 hexane:ethyl ether. The combined organic layer was washed with 10% sulfuric acid, brine, and water. Stored in refrigerator.

The following Example VI is shown for producing a preferred isomer of 9(Z),11(E)-CLA containing 75% of the desired isomer accompanied by the 9(Z),11(Z)-isomer.

EXAMPLE VI 12 g (0.0384 mol) methyl ricinoleate were dissolved in 30 ml pyridine, and 10.5 g tosyl chloride were added. The mixture was left overnight at room temperature. An abundance of crystals were observed. 200 ml water and 150 ml hexane were added. The hexane layer was washed with 2×100 ml dilute acetic acid, 3×100 ml water, 1×100 ml brine, and then it was dried and evaporated: 16.8 g (100%) tosylate.

Dissolved in 70 ml acetonitrile, and 11.7 g (0.0768 mol) DBU (diazabicycloundecene) were added. After 3 hours at room temperature, 20–30% was reacted (TLC). After 15 hours, about 60% was reacted. Heated to 75–80° C. for 30 minutes, 90% reacted. After 2 hours at 75–80° C., all reacted and worked up. Poured into water, extracted with hexane (100 ml), washed with dilute acetic acid, water, and brine, evaporated: 9.0 g slightly yellow oil.

Repeated tosylate, worked up the same way, reacted with DBU as above for 11 days at approximately 12° C. All reacted from starting material. Gas Chromatography (GC) shows 78.51% 9(Z),11(E)-CLA and 17.14% 9(Z),11(Z)-CLA 10.36 g (91%) yield. Identifications of the isomers were confirmed by independent University analyses, using standards obtained from bacterial formation of CLA.

The gas chromatography printout from the product of Example VI is shown in FIG. 1.

Example VI shows the reaction of methyl ricinoleate tosylate with DBU in acetonitrile. In the first step, only tosyl chloride was used. It is preferred for the elimination purpose. Iodide can also be used. For example, sulfonyl ester group can be replaced by iodide. However, oxygen is excluded since traces of elemental iodine can isomerize double bonds which is undesirable in the novel synthesis as used in the method of the present invention. Methane sulfonyl chloride also can be used. In the first step, pyridine is preferred as solvent and as base to neutralize the HCl produced in the reaction. Other solvents work much less completely and much more slowly.

In the second step, DBN or DBU is essential. Other bases have not worked. Particularly important is the use of bases that cannot cause substitution. Sodium hydroxide has been used previously on the chloride, not the tosylate, but a mix of isomers results in which the trans, trans [9(E),11(E)] isomer was the only one isolated in pure form.

The preferred solvent for the second step is acetonitrile, although others, such as THF and toluene, also work but require higher temperatures and/or longer reaction times.

The mechanism is E2 elimination mechanism for the most part. Pure E2 would require exclusive formation of the 9(Z),11(E)-isomer. Finding 17% of the 9(Z),11(Z)-isomer shows that about 34% of the reaction forms at first a carbocation which equilibrates and leads to 17% 9(Z),11 (Z)-isomer and 78% 9(Z), 11(E) isomer.

In accordance with the present invention, I have produced the cis-9, trans-11 isomer [9(Z),11(E)-isomer] and have verified independently that the main (78%) product is indeed the cis-9, trans-11 isomer [9(Z),11(E)-isomer], and that the minor (17%) product is the cis-9, cis-11-isomer [9(Z),11(E)-isomer]. Independent University analyses have identified these two peaks in gas chromatography (GC) traces. The independent University analyses used standards from bacterial produced CLA.

I also have found and shown a chemical proof.

Both compounds have two double bonds. I used a reaction which reduces one double bond at a time.

I then identified the three compounds with one double bond each and the compound with no more double bonds (stearic acid ester). The reaction was developed for unconjugated double bonds, and I have found it works as well with the conjugated double bonds.

Figure 2:
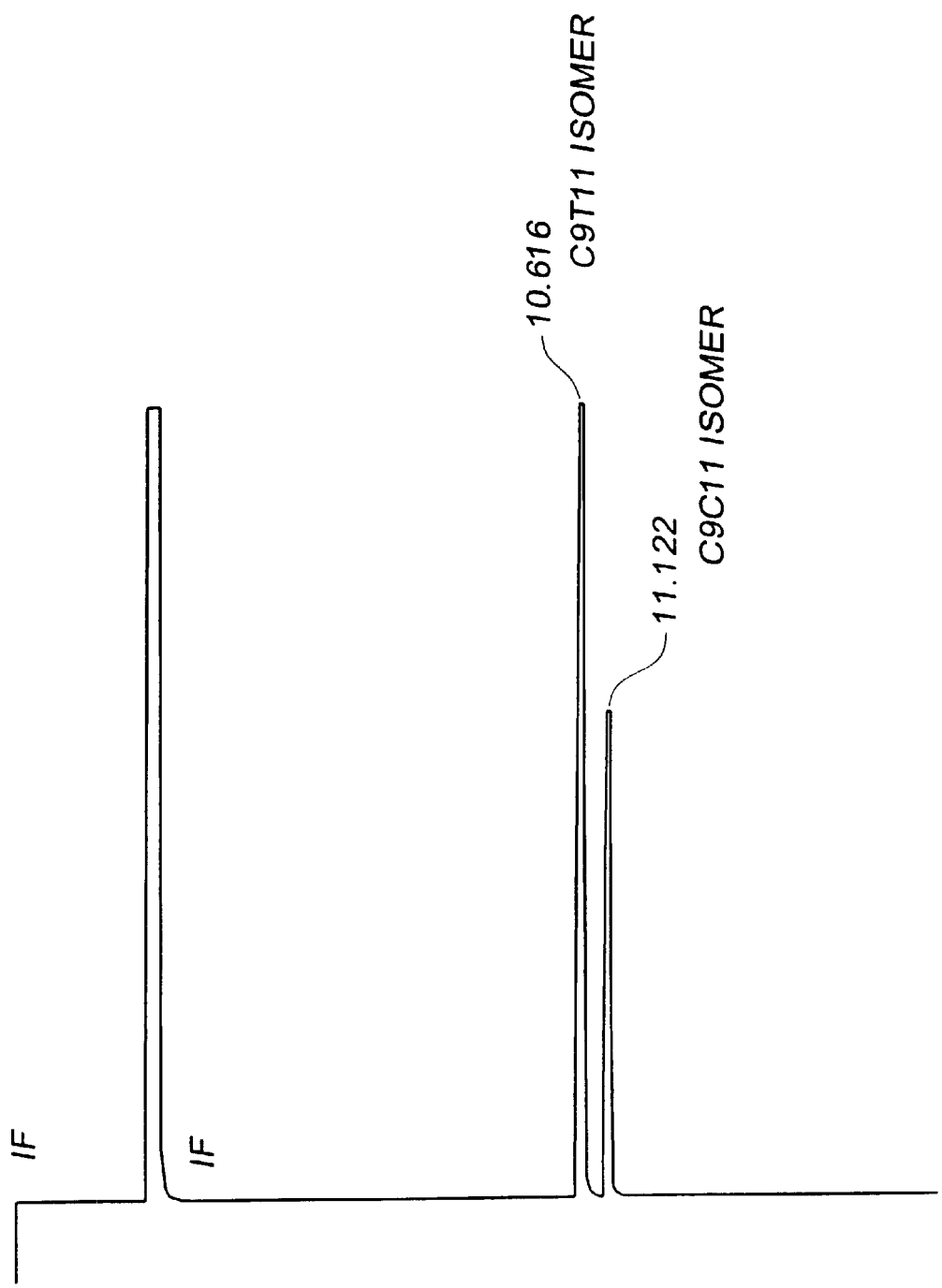
FIG. 2 is a graphical view of a gas chromatography printout of the starting material of the chemical analysis of CLA produced by a novel synthesis for purified CLA used in the method of the present invention.

FIG. 2 shows the starting material mixture (GC trace). The peak at 10.616 is the cis-9, trans-11 isomer. The smaller peak at 11.122 is the cis-9, cis-11 isomer. On reducing one double bond and then the other, the following reactions will take place.

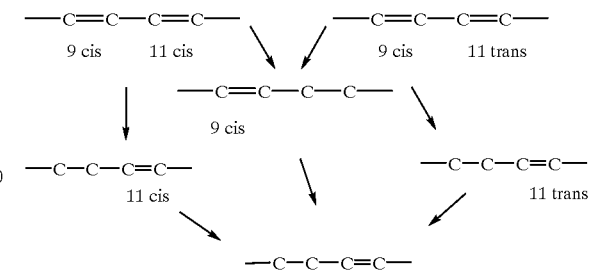

Hence as the reaction proceeds, twice as much cis-9 ester is formed as the others together, and since the starting material has five times as much cis-9, trans-11 than cis-9, cis-11, more trans-11 is formed than cis-11. Eventually, stearic ester predominates.

The chemical proof is performed and shown in Example VII.

EXAMPLE VII 550 mg of a CLA sample which by GC was 74% methyl 9(Z),11(E)-octadecadienoate and 25% methyl 9(Z),11(Z)-octadecadienoate were dissolved in 70 ml ethanol in a 250 ml three-neck flask equipped with thermometer and gas inlet and outlet tubes. A slow stream of oxygen was passed over the liquid which was heated to 40° C. with a heating mantle. One ml of 95% hydrazine was added and the temperature went to 45° 0C. and stayed there. Samples of 20 ml each were taken at 30 minutes and 60 minutes and the reaction stopped at 90 minutes. The samples were acidified with concentrated HCl and the solvents evaporated, 10 ml water added and extracted with 10 ml hexane. Hexane solutions were used for GC determinations.

Figure 3:
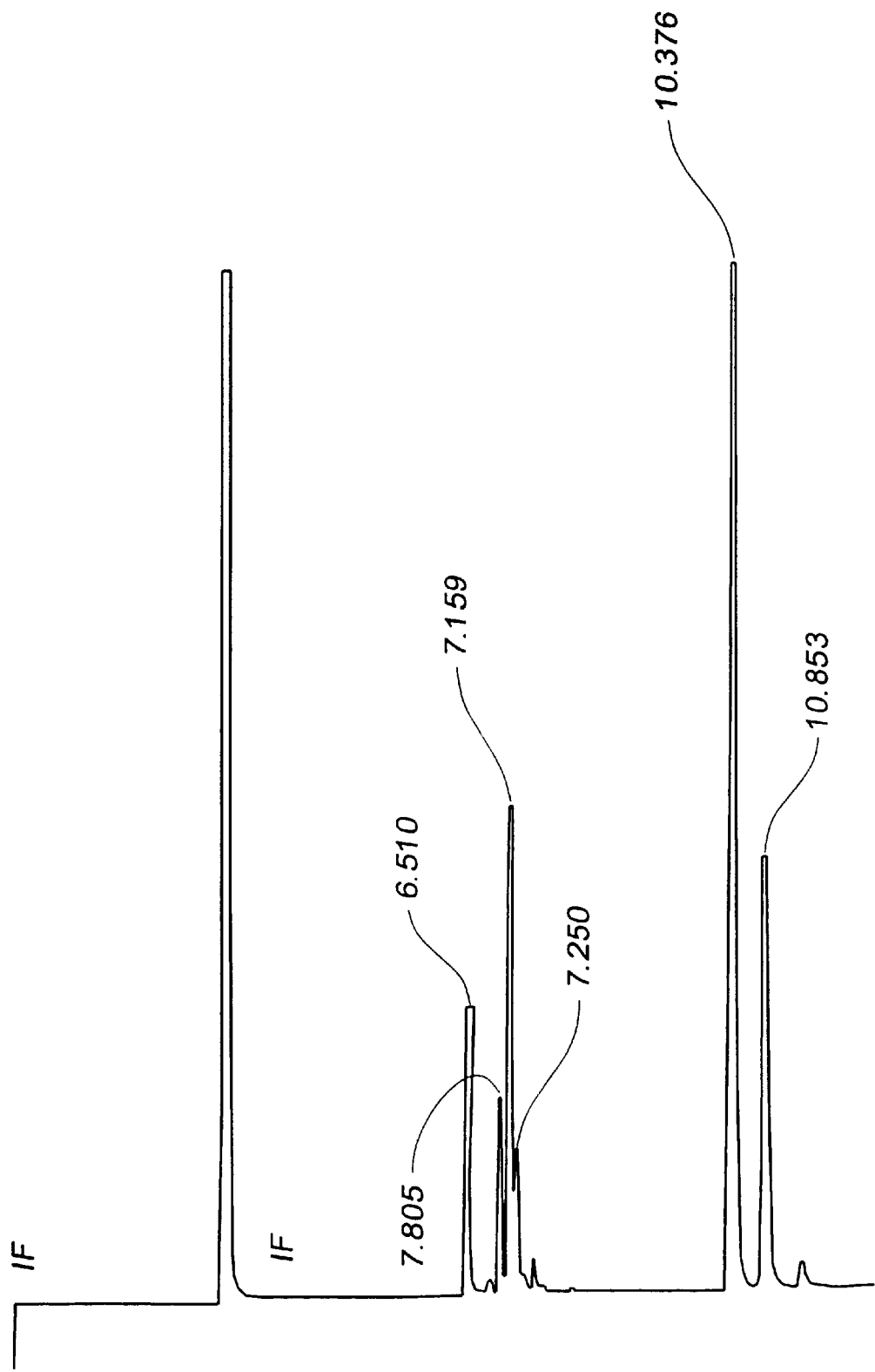
FIG. 3 is a graphical view of a gas chromatography printout at 30 minutes into the chemical analysis of CLA produced by a novel synthesis for purified CLA used in the method of the present invention.
Figure 4:
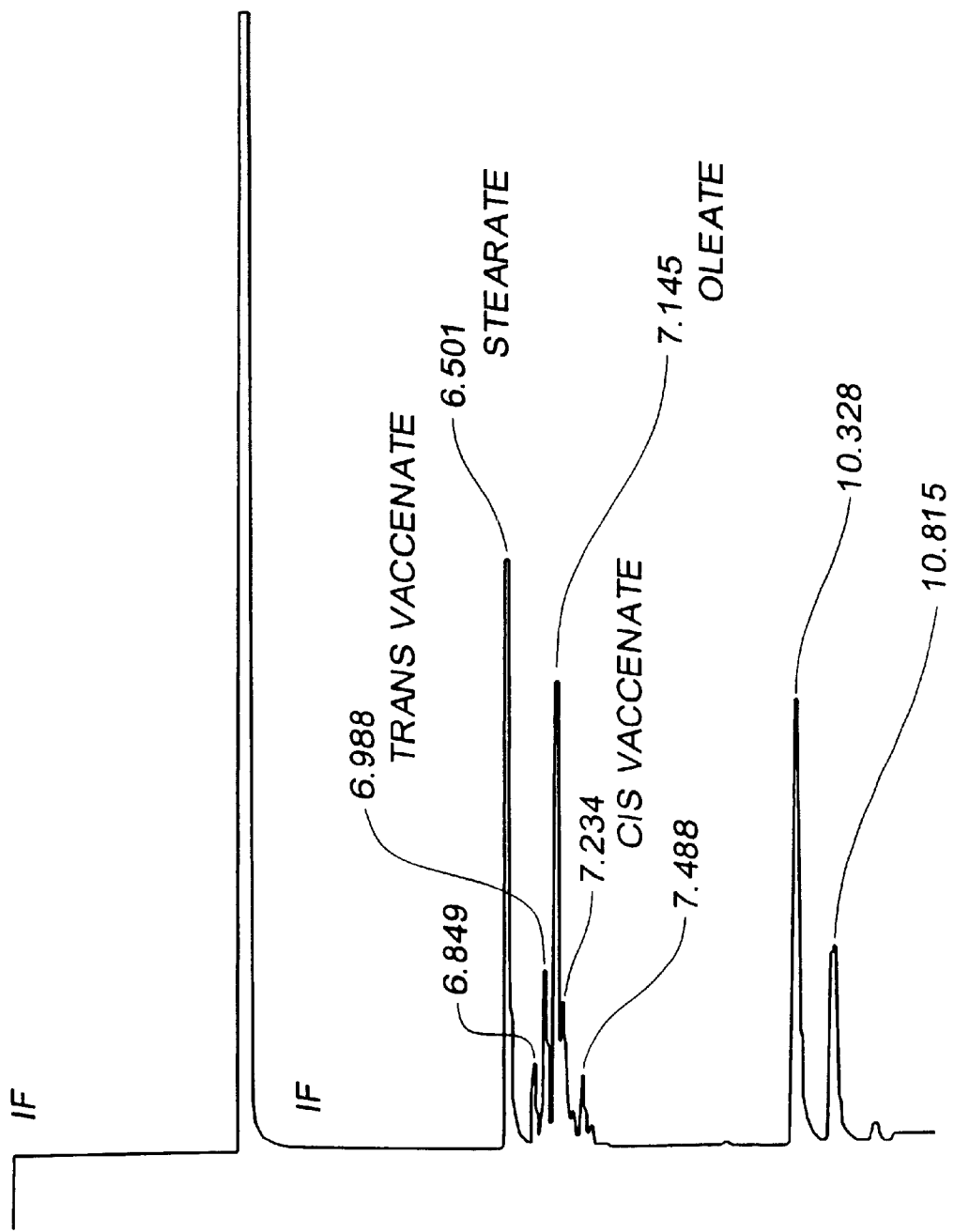
FIG. 4 is a graphical view of a gas chromatography printout at 60 minutes into the chemical analysis of CLA produced by a novel synthesis for purified CLA used in the method of the present invention.
Figure 5:
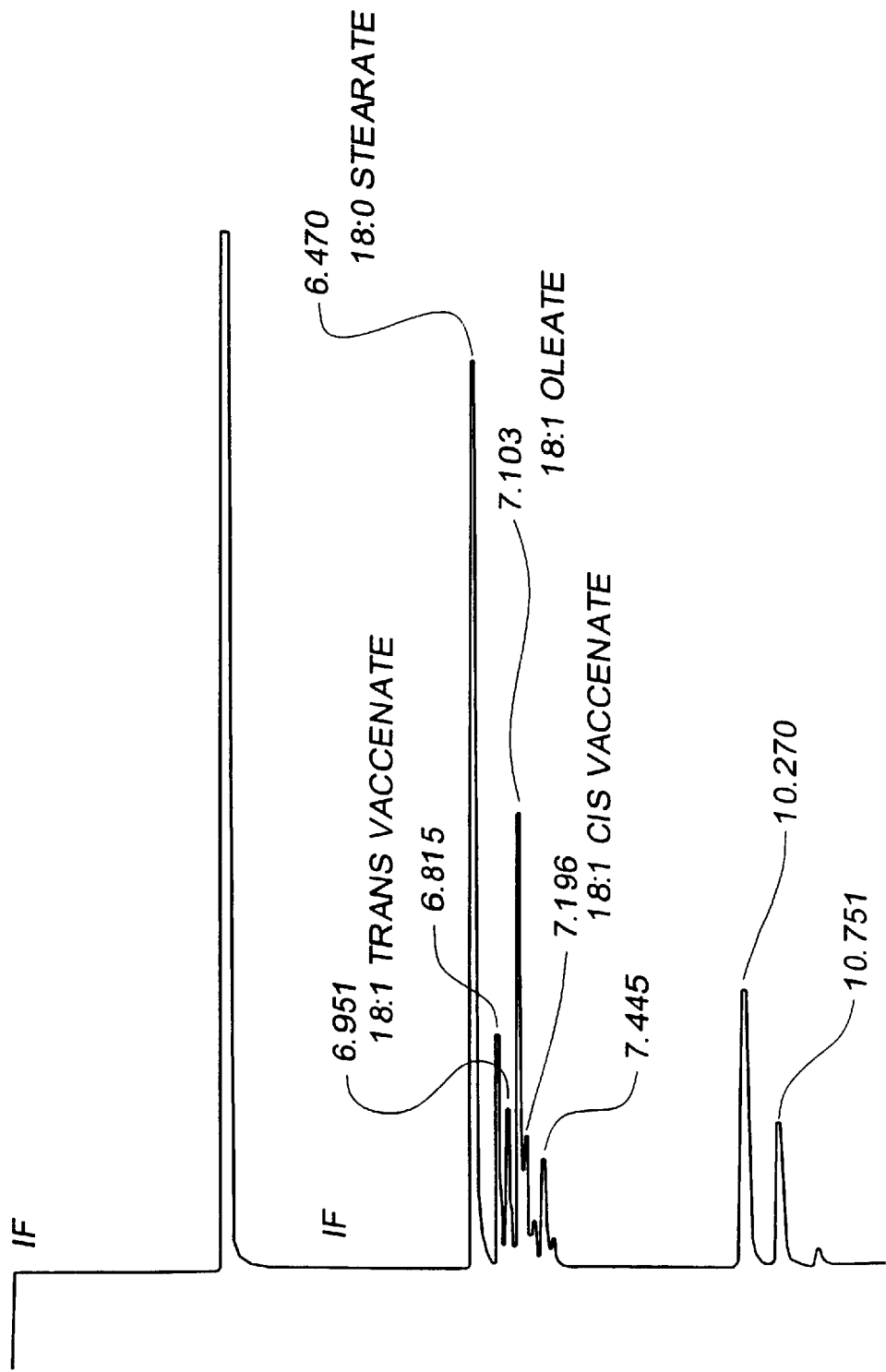
FIG. 5 is a graphical view of a gas chromatography printout at 90 minutes into the chemical analysis of CLA produced by a novel synthesis for purified CLA used in the method of the present invention.

FIG. 3 shows the reaction mixture after 30 minutes. Both starting materials are reduced in content, some stearic ester has been formed, and among the products, cis-9 (also called oleate) predominates. There is more trans-11 (also called trans vaccenate) than cis-11 (also called vaccenate). At 60 minutes (FIG. 4) and 90 minutes (FIG. 5), an analogous picture is seen; the starting materials are further diminished, and stearic ester becomes the biggest peak. For comparison, the traces for pure oleate, vaccenate, and trans vaccenate were run also. The GC technique does not always give absolute reproducibility, and hence pure compounds are done at the same time as the mixtures. The samples were run again on another column which pulled the peaks farther apart with similar results.

My novel synthesis produces octadecadienoic acid not by cooking the linoleic acid in base, but by eliminating water from a methyl lesquerolate.

I have been able to recrystallize the product acid at low temperature from ethyl ether and petroleum ether. After three recrystallizations, a 97% pure sample results which melts at 19–20° C.

The recrystallized product purity can be verified by the method according to which the acid has been made in the prior art as described by the very laborious method of Gunstone and Russell (*Chem. Soc.,* pp. 3782, 3787, 1955). These authors report a m.p. of 19–20.2° C.

A further development of my method avoids the use of pyridine and proceeds in one step from ricinoleate. Tosylation is done with p-toluenesulfonic anhydride, thereby avoiding any chloride in the mix which tends to produce substitution. The base is two moles of DBU. The solution contains the product and the salt of DBU and p-toluenesulfonic acid. This allows the easy regeneration of DBU and, if needed, that of p-toluenesulfonic acid. This reaction works well with castor oil itself. The product is a triglyceride with 90% CLA since castor oil is a triglyceride with 90% ricinoleic acid and 10% of a mix of oleic, linoleic, and the like acids.

Early work in the development of the novel synthesis of the present invention used methyl ricinoleate and phosphorylchloride yielded 12-chloro-ricinoleate. The 12-chloro-ricinoleate reacted with aqueous base or diazabicyclononene (DBN) yielded mixtures of CLA isomers. Accordingly, it was found that although phosphorylchloride was expected to be workable, it did not work. Chloride substitution of the hydroxyl was observed.

The reaction of the tosylate of methyl ricinoleate with reagents containing nucleophiles such as chloride ion, pyridine (or other nucleophilic amine) produced substitution rather than elimination.

Methyl ricinoleate reacted with Burgess' reagent, reputed to be a sure-fire reagent for splitting off water, showed no likely product by gas chromatography. Moreover, Burgess' reagent would be too expensive for a practical method.

The following actual examples describe the development of the novel synthesis of the present invention in detail.

EXAMPLE VIII

A. 1 g of ricinoleic acid methyl ester was refluxed in 30 ml acetic acid with 3 ml acetic anhydride added and 1 g of Amberlyst-15 as catalyst for 3 hours. Poured into 200 ml water and stirred for 30 minutes. Picked up in ether, ether layer washed with water and dried and evaporated. TLC shows new spot where oleate shows positive impurities and some starting material.

B. 1 g of methyl ricinoleate was treated with 3 ml acetic anhydride in 10 ml pyridine overnight. Poured into water and extracted with ether. TLC shows single spot higher than starting material (the acetate of ricinoleate). Product was refluxed for hours in 50 ml toluene with 1 g Amberlyst-15 as catalyst.

Evaporation after washing with water and adding of ether gave a clear oil with the same spot as A (cleaner reaction). Product of A+B was passed through silica column with hexane and "oleate" spot obtained pure: 800 ma. Gas chromatography showed bizarre mixture.

Amberlyst-15 is a sulfonic acid resin. Acid catalyzed splitting off of acetic acid from the acetate of ricinoleate produced complex mixtures.

EXAMPLE IX

To 15.6 g (0.05 mol) of methyl ricinoleate and 5 g (0.06 mol) pyridine in 100 ml methylene chloride was added 9.5 g (0.05 mol) p-toluene sulfonyl chloride. The solution remained clear, and the next morning very little reaction was seen by TLC (ether:pet ether 30:70). After another 24 hours, very little more reaction. Added 10 ml triethyl amine and 4 g more toluene sulfonyl chloride. Left standing over the weekend. Very red solution, some solid. Washed with water, 2 N HCl and 2×water. Dried and evaporated. Picked up in 200 ml hexane, and silica added till all the red color had been absorbed. Filtered and evaporated. TLC showed a little starting material, some almost at solvent front and most product a little ahead of starting material.

The 17 g product was dissolved in 100 ml methylene chloride and 7 g DBN (diazabicyclononene) added. After 12 hours, some increase in the top spot. After 5 days, about 50% was reacted. More DBN (2 g) was added and left standing for 2 weeks. Almost 90% top spot. Isolated by chromatography.

Tosylation with pyridine or triethylamine and tosyl chloride when heated leads to many side products because of substitution reactions of the amines with the intermediate tosylate.

Example IX shows an attempt to split off toluene sulfonic acid to make CLA.

The Example shows a partially successful preparation of the tosylate of methyl ricinoleate. The reaction was slow and incomplete, use of inappropriate solvent. The reaction product was reacted with DBN (an analog of the later used DBU). The right product was formed but incompletely. Wrong solvent again.

The reaction to make the toluene sulfonate intermediate does not go well in solvents other than pure pyridine. The reaction to split off the toluene sulfonate does not go well except in acetonitrile.

It was tried to get the toluene sulfonate intermediate with triethyl amine in acetonitrile. Even after a week at room temperature, the reaction was not complete. Heating is not advised since the chloride ion present will lead to substitution by this ion.

EXAMPLE X 15.6 g methyl ricinoleate (0.05 mol) were dissolved in 30 ml pyridine and with ice cooling. 7 g (0.046 mol) phosphorus oxychloride were added drop by drop over 30 minutes. Left at room temperature for 24 hours and then heated at 55° C. for 1 hour. Poured into a mixture of 100 ml water and 100 ml methylene chloride. Organic layer washed with 2×200 ml 1 N HCl and 3×100 ml water. Dried and filtered and evaporated. TLC shows fast moving spot which could be the CLA product and some starting material.

Example X shows a reaction of methyl ricinoleate with phosphorus oxychloride and pyridine. The product was shown later by gas chromatography to be 12-chloro-analog of methyl ricinoleate. That product tended to form whenever chloride ions were present. Substitution is favored over the desired elimination. Heating the toluene sulfonate in pyridine with pyridine hydrochloride present produced only the 12-chloro compound.

EXAMPLE XI 1.3 g methyl ricinoleate was dissolved in 15 ml acetonitrile, heated to about 50° C., and 1 g of Burgess salt of methoxycarbonylsulfamoyl)-triethyl ammonium hydroxide was added (equimolar amount). Refluxed for one hour. Poured into water and extracted with methylene chloride. TLC (ether:pet ether 30:70) showed major spot almost at solvent front. GC showed no methyl linoleate.

Example XI shows an attempt to dehydrate methyl ricinoleate with Burgess' salt. The reaction with Burgess' salt worked partially, right solvent. But many side products were also formed and Burgess' salt is too expensive for a practical process.

This Example XI produced the desired CLA since it was later found that the CLA isomers do come out of the GC later than the unconjugated methyl linoleate. However, Burgess' salt is far too expensive to provide a practical procedure at $45.70 (1996) for one g.

EXAMPLE XII

Methyl ricinoleate was prepared and converted to 12-chloro oleate by thionyl chloride.

Methyl 12-chloro oleate was treated with sodium hydroxide.

12-chloro compound was treated with DBN in methylene chloride over 3 days. The result was negative. The wrong spot gets bigger, but not by much.

Example XII shows an attempt to split off HCl from methyl 12-chloro oleate. Methyl 12-chloro-oleate was prepared in an attempt to work with a chloro-group instead of the hydroxy group of the ricinoleate. Attempts to eliminate the chloro-group with DBN were unsuccessful. The TLC analytical technique does not distinguish well between the chloro- and the product compound. Also, reaction too slow.

The reaction of the chloro-compound with sodium hydroxide gives a mix like the prior art method.

EXAMPLE XIII 10 g (0.032 mol) methyl ricinoleate were dissolved in 60 ml pyridine and 9.12 g (0.048 mol) tosyl chloride added. Left at room temperature overnight. TLC (E:PE 30:70) shows complete reaction (only spot at app. Rf=0.6). Refluxed for one hour. TLC shows complete reaction to spot at Rf=0.9. Worked up by treatment with water and hexane. Hexane layer washed with water, dried and evaporated: 6.4 g of oil, GC looks like 12-chloro compound.

Example XIII shows a reaction of methyl ricinoleate with toluene sulfonyl (tosyl) chloride in pyridine and subsequent refluxing.

EXAMPLE XIV

Same run to make the tosylate but used 60 ml hexane and 10 ml pyridine. Needed to be warmed to effect solution. Overnight at room temperature showed only approximately 30% reaction by TLC. Evaporated down to pyridine (at approximately 40° C.) and 30 ml pyridine added. All converted to tosylate overnight at room temperature. Worked up and half refluxed in 20 ml pyridine for 40 minutes. Poured into pet ether and water. Some oil formed between pet ether layer and water layer, pyridinium salt, care had not been taken to remove all pyridine. Yield of ester with Rf=0.9 was 1.1 g.

The other half was dissolved in acetonitrile and 4 g (0.032 mol) DBN (diazabicyclononene) added. Left at room temperature over the weekend. All reacted. Some of the same insoluble oil formed. Yield of Rf=0.9 pet ether soluble oil: 2.0 g.

Example XIV shows (1) tosylate forms easily only in pyridine as solvent. Tosylate in acetonitrile with basic ion exchange resins have been tried without any success. Example XIV shows (2) whenever chloride ions are present, substitution by them is preferred. Example XIV shows (3) the presence of any pyridine causes substitution by pyridine yielding the pyridinium toluene sulfonate. Since DBN cannot substitute and an ester had formed which moved to the solvent front in TLC, the elimination of the elements of toluene sulfonic acid takes place, and the product was CLA.

Example XIV shows success in the first step. Tosylation is complete without side products when carried at room temperature in pyridine as solvent.

The elimination to form the desired product takes place on refluxing in pyridine. A lot of side product was observed. The easily separable pyridinium salt formed because of substitution of the tosyl group by pyridine.

EXAMPLE XV 5 g (0.016 mol) methyl ricinoleate was tosylated, worked up with dilute acetic acid (to remove all pyridine), water and brine. Dried and evaporated and dissolved in 50 ml tetrahydrofuran (THF) and 4 g DIPFEA added. Left over the weekend: no reaction. Refluxed for 1 hour, no change. Cooled and 3.4 g DBN added. Left overnight at room temperature. Not much reacted. Refluxed for 4 hours: approximately 45% was reacted. Solvent evaporated and 20 ml acetonitrile added. Refluxed for 45 minutes. All converted (by TLC).

Example XV shows an attempt to do the elimination with a hindered base of diisopropylethylamine which cannot do a substitution like pyridine. No reaction was seen. With some DBN, some reaction was observed. A more polar solvent is needed, and the tetrahydrofuran was determined not to work. With acetonitrile, on heating, a complete reaction was quickly achieved. The products were submitted to gas chromatography, and the cat 75:20 ratio of product to side product with otherwise few side products was seen.

Example XV shows solvents other than acetonitrile do not work at room temperature. Organic bases other than DBN and DBU do not eliminate properly. DBU is less expensive but otherwise analogous to DBN.

DBN was used in toluene. It was done at reflux (120° C.) and then gave a CLA mixture. Thus, DBN or DBU use is essential for success. Use of acetonitrile as solvent is preferred by a large margin.

EXAMPLE XVI 6.0 g of methyl ester of Example VI was saponified with sodium hydroxide in methanol, overnight at room temperature. The acid was isolated by acidifying and extracting. It solidified at dry ice temperature but liquefied at 10° C. From it, 97% (GC) pure 9(Z),11(E)-isomer acid of m.p. 19–20° C. was isolated by recrystallizing in the dry ice chest, twice from pet ether and once from ethyl ether.

Example XVI shows the preparation of the free acid from CLA methyl ester. Example XVI shows the preparation of the free acid from the ester and the first recrystallization of the acid and proof that purity can be increased that way.

EXAMPLE XVII

The tosylate was prepared as in Example VI, starting with 12 g methyl ricinoleate. The tosylate was dissolved in dimethyl sulfoxide (DMSO), 30 ml, and 11.7 g of diazabicyclo-undecene (DBU) was added.

After 7 hours, TLC (pet. ether: ethyl ether 70:30) showed approximately 40% completion; after 20 hours, approximately 60% done. Left at room temperature for 7 days: approximately 95% done; two layers had formed.

The product was not soluble in DMSO. The lower, DMSO, layer was yellow. The top layer was colorless.

Poured into 100 ml water and 100 ml hexane. The hexane layer was washed with 50 ml 1 N HCl, 100 ml water and 100 ml brine. There was a small amount of yellow liquid between the layers which was also discarded.

The hexane layer was dried and evaporated: almost colorless oil, 9.6 g (84%). By gas chromatography, oil was 77.1% 9(Z),11(E)-CLA and 19.0% 9(Z),11(Z)-CLA.

Example XVII shows the elimination of toluene sulfonic acid from tosylated methyl ricinoleate in DMSO as solvent.

DMSO may be a less objectionable solvent than acetonitrile. Also, the separation of the product from the reaction mixture makes workup easier. The workup described in Example XVII with water and hexane is not be necessary for large scale runs.

EXAMPLE XVIII

To a solution of 243.7 g (0.781 mol) of methyl ricinoleate in 900 ml acetonitrile was added dropwise over 2 hours a solution of 77 ml (114 g, 1 mol) of methane sulfonyl chloride in 192 ml acetonitrile. After 1 hour at room temperature, the resulting mixture was vacuum filtered, and most of the solvent was removed from the filtrate by vacuum evaporation. Water (300 ml) and a 50:50 mix of hexane and ethyl ether (300 ml) was added, and the upper layer was separated and washed with brine (2×200 ml). Dried with sodium sulfate and the solvents evaporated.

The same reaction was carried out with 257 g of methyl ricinoleate, and both batches were combined for vacuum distillation at 5 Torr: Fractions: (1) 33.3 g (2) 70.3 g (3) 212 g (4) 35.7 g.

Fractions (1), (2), and (3) came over at 173–174° C. Fraction (4) at 174–185° C. The content of fractions (1), (2), and (3) was the same: 75–77% 9(Z),11(E)-CLA, 15–17% 9(Z),11(Z)-CLA. Fraction (4) had appreciable amounts of 9(E),11(E)-CLA and was discarded. The total yield of acceptable product for fractions (1), (2), and (3) was 315.6 g (66%).

Example XVIII shows methane sulfonyl group as the leaving group instead of the p-toluene sulfonyl group. With some changes in the procedure, including no pyridine as solvent in the first step, this method worked as well and gave a lesser yield of an almost identical product mix: 75–77% 9(Z),11(E)-CLA and 15–17% 9(Z), 11(Z)-CLA.

EXAMPLE XIX

A chromatography column was filled with 5 liters of a specified strong acid macroreticular ion exchange resin exhaustively treated with silver ions in the form of silver nitrate. A feed of 35 g of 68% pure 9(Z),11(Z)-CLA methyl ester was passed through the chromatography column. In one pass, the first product out of the column was analyzed and found to be 17 g of 99% pure 9(Z),11(Z)-CLA methyl ester.

The novel synthesis as used in the method of the present invention is a novel synthesis of conjugated fatty acid. In one aspect, the novel synthesis as used in the method of the present invention includes a novel synthesis of a specific form of conjugated fatty acid, a specific isomer of CLA. The specific isomer of the present invention is 11-cis, 13-trans eicosadienoic acid, also known as 11(Z),13(E)-eicosadienoic acid.

It is believed that the presumptive active ingredient of conjugated octadecadienoic acid is provided by 11-cis, 13-trans eicosadienoic acid.

The importance of my novel synthesis is not only in the raising of lean animals but also in the potential as a cancer drug. Human trials have not been considered before a sufficient quantity of a pure preparation of 11-cis, 13-trans eicosadienoic acid was at hand.

The novel synthesis as used in the method of the present invention provides the first practical method for the preparation of 11-cis, 13-trans eicosadienoic acid or 11(Z),13(E)-CEA in high yield.

The novel synthesis as used in the method of the present invention produces the preferred isomer by splitting water off from lesquerolic acid. Elimination of water produces an (E)-double bond at the 13,14 position while keeping the 11,12(Z)-double bond of the lesquerolic acid.

The purified conjugated fatty acid of the present invention is useful in the treatment of carcinoma in a human through the steps of administering to a human a therapeutically effective amount of the purified 11-cis, 13-trans eicosadienoic acid formed by reacting a methyl lesquerolate with a tosyl chloride or a mesyl chloride to form a tosylate or mesylate of a methyl lesquerolate, reacting the tosylate or mesylate of a methyl lesquerolate with diazabicycloundecene, and purifying the synthesized 11-cis, 13-trans eicosadienoic acid using chromatography.

The purified conjugated fatty acid of the present invention has a significant potency relative to other fatty acids in respect to an ability to modulate tumorigenisis.

The method of the present invention provides treatment of and suppression of diabetes in a human through the steps of administering to a human a therapeutically effective amount of 11-cis, 13-trans eicosadienoic acid formed by reacting a methyl lesquerolate with a tosyl chloride or a mesyl chloride to form a tosylate or mesylate of a methyl lesquerolate, and reacting the tosylate or mesylate of a methyl lesquerolate with diazabicycloundecene.

The method of the present invention provides treatment of and suppression of arthritis in a human through the steps of administering to a human a therapeutically effective amount of 11-cis, 13-trans eicosadienoic acid formed by reacting a methyl lesquerolate with a tosyl chloride or a mesyl chloride to form a tosylate or mesylate of a methyl lesquerolate, and reacting the tosylate or mesylate of a methyl lesquerolate with diazabicycloundecene.

The method of the present invention provides treatment of and suppression of allergies and allergic reactions in a human through the steps of administering to a human a therapeutically effective amount of 11-cis, 13-trans eicosadienoic acid formed by reacting a methyl lesquerolate with a tosyl chloride or a mesyl chloride to form a tosylate or mesylate of a methyl lesquerolate, and reacting the tosylate or mesylate of a methyl lesquerolate with diazabicycloundecene.

The method of the present invention provides treatment of and suppression of inflammation in a human through the steps of administering to a human a therapeutically effective amount of 11-cis, 13-trans eicosadienoic acid formed by reacting a methyl lesquerolate with a tosyl chloride or a mesyl chloride to form a tosylate or mesylate of a methyl lesquerolate, and reacting the tosylate or mesylate of a methyl lesquerolate with diazabicycloundecene.

Thus, it can be seen that the present invention accomplishes all of the stated objectives.

Although the invention has been illustrated by the preceding detailed description, it is not intended to be construed as being limited to the specific preferred embodiments employed therein.

Whereas particular embodiments of the invention have been described herein above, for purposes of illustration, it will be evident to those skilled in the art that numerous variations of the details may be made without departing from the invention as defined in the appended claims.

What is claimed is:

1. A synthesis process for producing a conjugated fatty acid, comprising:

(a) providing a fatty acid ester having somewhere in its carbon chain a chain of four carbon atoms such that carbon one bears one hydrogen and one hydroxyl group, carbon two bears two hydrogen atoms, and a double bond is positioned between carbon three and carbon four, and reacting with a chloride selected from the group consisting of toluenesulfonyl chloride, methanesulfonyl chloride, benzenesulfonyl chloride, alkylsulfonyl chloride, and arylsulfonyl chloride at a temperature in the range of 10–100° C. to form a sulfonyl ester; and (b) providing a conjugated fatty acid ester bearing said sulfonyl ester reacted with diazabicyclo-undecene, said conjugated fatty acid having a purity greater than 40%.

2. A synthesis process as set forth in claim 1, wherein said reacting with a chloride comprises reacting at temperature in the range of 20–50° C.

3. A synthesis process as set forth in claim 1, wherein said reacting with a chloride comprises reacting with toluenesulfonyl chloride or methanesulfonyl chloride, at temperature in the range of 20–50° C.

4. A synthesis process as set forth in claim 1, wherein said reacting with a chloride comprises reacting in a pyridine solvent.

5. A synthesis process as set forth in claim 1, wherein said reacting with diazabicyclo-undecene comprises reacting in a polar, non-hydroxylic solvent.

6. A synthesis process as set forth in claim 5, wherein said polar, non-hydroxylic solvent comprises acetonitrile.

7. A synthesis process as set forth in claim 1, wherein said conjugated fatty acid has a purity greater than 50%.

8. A synthesis process as set forth in claim 1, wherein diazabicyclononene is used in place of said diazabicyclo-un-decene.

9. A synthesis process as set forth in claim 1, wherein said sulfonyl ester group is replaced by iodide.

10. A synthesis process as set forth in claim 5, wherein said polar, non-hydroxylic solvent comprises THF or toluene.

11. A synthesis process as set forth in claim 1, wherein said reacting with a chloride to form a sulfonyl ester comprises reacting with p-toluene sulfonic anhydride.

12. A synthesis process as set forth in claim 1, wherein said reacting with a chloride to form a sulfonyl ester comprises reacting with methane sulfonyl chloride.

13. A synthesis process as set forth in claim 5, wherein said polar, non-hydroxylic solvent comprises ethyl acetate or dimethyl sulfoxide.

14. A synthesis process as set forth in claim 1, wherein said reacting with a chloride to form a sulfonyl ester comprises reacting with mesyl chloride.

15. A synthesis process as set forth in claim 14, wherein said reacting with mesyl chloride comprises reacting with mesyl chloride in acetonitrile and triethyl amine.

16. A synthesis process as set forth in claim 15, wherein reacting with diazabicyclo-undecene comprises mesylate reacted with diazabicyclo-undecene in a polar, non-hydroxylic solvent.

17. A synthesis process for producing a conjugated fatty acid, comprising:

(a) reacting a chloride selected from the group consisting of toluene sulfonyl, methane sulfonyl, benzene sulfonyl, alkylsulfonyl, and arylsulfonyl at a temperature in the range of 10–100° C. with an acid or ester having somewhere in its carbon chain a chain of four carbon atoms such that carbon one bears one hydrogen and one hydroxyl group, carbon two bears two hydrogen atoms, and a double bond is positioned between carbon three and carbon four to form an intermediate ester; and (b) reacting said intermediate ester with a compound selected from the group consisting of diazabicycloundecene and diazabicyclononene at room temperature in a second solvent of a compound selected form the group consisting of acetonitrile, toluene, tetrahydofuran, and dimethylsulfoxide to form conjugated fatty acid in high yield.

18. A synthesis process for producing conjugated fatty acid as set forth in claim 17, wherein said high yield is greater than 40%.

19. A synthesis process for producing conjugated fatty acid as set forth in claim 18, wherein said high yield is greater than 50%.

20. A synthesis process for producing conjugated fatty acid, comprising:

(a) reacting a tosylate or mesylate with methyl ester having somewhere in its carbon chain a chain of four carbon atoms such that carbon one bears one hydrogen and one hydroxyl group, carbon two bears two hydrogen atoms, and a double bond is positioned between carbon three and carbon four at a temperature in the range of 20 degrees Centigrade to 50 degrees Centigrade in a solvent of pyridine to form a tosylate or a mesylate; and (b) reacting said tosylate or mesylate with diazabicycloundecene at a temperature in the range of 20 degrees Centigrade to 50 degrees Centigrade in a solvent of acetonitrile to form conjugated fatty acid in a yield higher than about 50%.

* * * * *